United States Patent [19]

Quimby, Jr.

[11] Patent Number: 4,902,333
[45] Date of Patent: Feb. 20, 1990

[54] CONTROL OF UNDESIRABLE VEGETATION

[75] Inventor: Paul C. Quimby, Jr., Leland, Miss.

[73] Assignee: The United States of America as represented by the Secretary of Agriculture, Washington, D.C.

[21] Appl. No.: 114,952

[22] Filed: Oct. 30, 1987

[51] Int. Cl.$^4$ .............................................. A01N 63/04
[52] U.S. Cl. ........................................... 71/79; 71/92; 71/108; 71/120; 71/DIG. 1
[58] Field of Search ................... 71/79, DIG. 1

[56] References Cited

U.S. PATENT DOCUMENTS

| | | | |
|---|---|---|---|
| 2,465,335 | 3/1949 | Burkhard | 71/DIG. 1 |
| 2,868,688 | 1/1959 | Benesi et al. | 71/DIG. 1 |
| 2,976,210 | 3/1961 | Cosby et al. | 71/DIG. 1 |
| 3,197,299 | 7/1965 | Stull et al. | 71/DIG. 1 |
| 3,776,857 | 12/1973 | Linder | 71/DIG. 1 |
| 4,263,036 | 4/1981 | Charudattan | 71/79 |
| 4,718,935 | 1/1988 | Walker et al. | 71/79 |

FOREIGN PATENT DOCUMENTS 0703607 2/1965 Canada ........................... 71/DIG. 1

OTHER PUBLICATIONS

The Merck Index, 10th edition, 1983, pp. 37, 38, 229, 779 and 780.

Primary Examiner—Glennon H. Hollrah
Assistant Examiner—Susan P. Treanor
Attorney, Agent, or Firm—M. Howard Silverstein; John D. Fado

[57] ABSTRACT

Fungal pathogen is applied to weeds in such a manner that misting or an extended dew period is not necessary to germinate and grow the fungus. In particular, an oil-in-water invert emulsion containing a special additive is applied to the weeds at the same time or immediately after application of the fungal pathogen, wherein the special additive is (a) wax or (b) lecithin in combination with a calcium salt. Lecithin particularly is effective as an emulsifying agent for forming the emulsion, and for forming invert emulsions for applying chemical herbicides to weeds.

19 Claims, No Drawings

CONTROL OF UNDESIRABLE VEGETATION

FIELD

This invention relates to new formulations and methods for controlling vegetation such as weeds.

PRIOR ART

The following fungi are known to be useful as plant pathogens against a number of weeds: *Colletotrichum gloeosporioides; Colletotrichum malvarum; Fusarium lateritum; Fusarium solani; Alternaria macrospora; Alternaria cassiae; Alternaria crassa.* The uses of these pathogens against weeds are disclosed in the following references:

Pat. Nos. 3,849,104, 3,999,973, 4,390,360;
Weed Science v. 29, pp. 629–631, 1981, H. L. Walker;
Weed Science v. 29, pp. 505–507, 1981, H. L. Walker;
copending application Ser. No. 92,100, filed Sept. 2, 1987, Boyette et al.

It has been shown that these fungi normally do not infect the target weeds unless exposed to several hours of dew or free moisture after application.

SUMMARY

I now have discovered a spray formulation for applying water to undesirable vegetation at the same time or immediately after application of fungal pathogen, whereby the water remains in contact with the fungus, thus enabling the fungus to germinate and grow without the need for dew or misting. The formulation comprises an invert emulsion, i.e., water-in-oil, containing a special additive. It is thought that the intimate contact between the water and oil in the emulsion, in the presence of the special additive, enables the water to reach the target and remain thereon with minimal loss through evaporation, thereby supplying the necessary moisture for fungal germination and growth.

The special additive of the present invention consists of one or both of the following: (a) a wax or (b) the combination of lecithin and calcium salt such as calcium chloride or calcium acetate. The additive is important because the use of oil per se in the emulsion essentially does not result in fungal germination and growth.

It further has been discovered that lecithin is particularly effective as an emulsifier for the invert emulsion, and that lecithin-emulsified invert emulsions are especially easy to formulate and may be used for purposes other than application of fungal pathogens such as the application of chemical herbicides to vegetation. In this embodiment, the above-described special additive is not necessary.

Therefore, it is an object of the present invention to provide a new method of application of fungal pathogen to undesirable vegetation.

Another object is to provide a new formulation for applying control agents including fungal pathogens and/or chemical herbicides to vegetation.

A further object is to apply fungal pathogens to vegetation which does not require dew or misting for activation purposes.

A still further object is to provide a new formulation for applying fungal pathogens to vegetation which does not require dew or misting to activate the fungus.

DETAILED DESCRIPTION

Any oil which is compatible with the fungal pathogen or chemical agent to be applied to the target vegetation may be employed to produce the invert emulsion of the present invention. Suitable oils for many fungal pathogens include: heavy mineral oil, light paraffinic oil, soybean oil, tung oil, peanut oil, cottonseed oil, corn oil, or combinations thereof. A water-oil volume ratio of about 1:3–2:1, preferably 1:3–6:5, is suitable. The amount of water that is incorporated into the invert emulsion may be increased by allowing the two phases to stand for several hours after mixing.

The emulsifying agent for the invert emulsion must be compatible with the fungal pathogens being applied to the vegetation. Lecithin and casein are suitable in most instances, lecithin being preferred. A lecithin concentration of about 10 to 120 grams per liter of emulsion generally is suitable, preferably 30 to 110 grams per liter.

Paraffin wax is the preferred wax additive although beeswax and natural plant wax may be used. The wax additive should be about 20 to 80 grams per liter. Ordinarily, the wax is melted into the heated oil component, and thereafter cooled to room temperature. In the case of employing calcium salt in combination with the above amounts of lecithin as additive, the calcium salt should be present in an amount of about 1 to 3 grams per liter of emulsion. The preferred calcium salt is calcium chloride. With regard to the combination of calcium salt and lecithin, it is thought that a complex is formed therebetween which acts in a manner similar to the wax in enabling the oil-plus-additive to trap water in contact with the fungus.

When both additives are present in the formulation, the amount of each additive may be reduced from the above figures depending upon its relative presence.

As a further modification, calcium hydroxide may be suspended in the formulation in an amount of about 2.5–25 grams per liter, preferably about 2.5–5.0 grams per liter, for the purpose of trapping carbon dioxide in the deposit and maintaining a more basic pH for enhancing stomatal openings in the leaves of target weeds and thereby enhancing fungal hyphae penetration.

All the above-enumerated fungal pathogens may be employed in the practice of the present invention. Any fungus is suitable which is physically and chemically compatible with the emulsion oil, emulsifying agent and additives.

The method of the present invention may be carried out in one or two steps. In the one-step procedure, the fungal pathogen is a component of the emulsion, and the emulsion is sprayed onto undesirable vegetation such as weeds. In the two-step method, the fungal pathogen first is sprayed on the weeds from an aqueous suspension; and immediately thereafter (i.e., within about 30 seconds or less) the invert emulsion without pathogen is applied. In an alternate two-stepprocedure, an aqueous carrier (without fungal pathogen) is sprayed on target foliage, followed by an immediate application of invert emulsion containing the pathogen.

The manner of producing spores or mycellium of fungal pathogens for incorporation into the invert emulsion, or for suspension in an aqueous carrier in those instances when the invention is practiced in a two-step manner, is known in the art, as described in the above-cited literature, patents and co-pending patent application.

In the two-step method of practicing the present invention, wherein the fungus is suspended in an aqueous carrier, typical concentrations of spores in the carrier may be $10^3$–$10^6$ spores per ml of carrier. An optional additive for the carrier is sodium alginate as a thickener-humectant, in an amount of about 2.5 –10 grams per liter, preferably about 2.5 grams per liter. Another optional additive is corn syrup to help prevent plasmolysis, and to serve as an energy source for growing fungus, at a typical concentration of about 5 ml per liter of carrier. Surfactants such as liquid or bar soap preferably are employed with the carrier in a very small amount, e.g., about 0.01–0.5 ml or gram per 100 ml of carrier, to help ensure contact of the aqueous carrier with waxy leaf surfaces on the target vegetation. Typical application rates of the aqueous suspension of the fungus to the target vegetation are about 20–100 gallons, preferably about 80–100 gallons, per acre.

In the one-step method of the present invention, spores or mycelium of the fungus are mixed into the invert emulsion usually in a higher concentration (usually four or more times greater) than in the aqueous carrier in the two-step mode because much smaller quantities of invert emulsion are applied to the target substrate.

Whether the invert emulsion is applied as part of the one-or two-step method, an air-assist spraying system may be employed to apply same in order to form droplets that are large enough to produce deposits greater than 650 microns in diameter on the vegetation. Application rates of the invert emulsion may range from about 1-100 gallons per acre. Typical application rates are about 1-24 gallons per acre, preferably about 3-12 gallons per acre. The emulsion can be applied on a band over the area where a valuable crop is planted (e.g., the "drill area"). The band width may vary from 10–20 inches depending upon the width of the crop row and the width to be mechanically cultivated to control those weeds outside the treated part of the row over the "drill area." Since this method involves application to only a fraction of the total area planted to the crop, the amount of material is reduced proportionally for that total crop area. For example, if rows are 40 inches wide and the treated band is ⅓ of the row, then an application volume of 12 gallons per treated area would require 4 gallons per total crop area.

Sodium alginate and/or corn syrup may be employed as additives in the fungus-containing invert emulsion.

As an alternative embodiment either in the one- or two-step practice of the present invention, chemical herbicides compatible with the fungal pathogens, such as linuron, imazaquin, or lactofen may be added to the invert emulsion so as to apply both the fungal pathogen and chemical herbicide to the undesirable vegetation.

As noted in the Summary, lecithin particularly is effective as an emulsifying agent for the invert emulsion, and such lecithin-containing emulsions, even without wax or calcium salt additive, may be employed to apply chemical herbicides in general (in the absence of fungal pathogen). Typical herbicides for incorporation therein include glyphosate for control of johnsongrass, lactofen for control of cocklebur, 2-4-D for control of eurasian watermilfoil. The concentration of the chemical agents in the emulsion will depend upon such factors as spray volume per unit area, and degree of infestation of the undesirable vegetation.

In addition to controlling undesirable vegetation, the emulsions of the present invention may be used to evaluate host resistance of economically important crop species to pathogens or for evaluating fungicides.

I claim:

1. In a method of applying a herbicidally effective amount of fungal pathogen to undesirable host vegetation, the improvement comprising spraying an additive-containing invert water-in-oil emulsion on said vegetation at the same time or immediately after application of said fungal pathogen to enable water which reaches said vegetation to remain thereon with minimal loss through evaporation, thereby supplying necessary moisture for fungal germination and growth, said oil being compatible with said pathogen, said additive selected from the group consisting of (a) a wax selected from the group consisting of paraffin wax, beeswax, and natural plant wax, (b) lecithin in combination with calcium chloride or acetate, and (c) mixtures of (a) and (b).

2. The method of claim 1 wherein said additive is calcium chloride and lecithin.

3. The method of claim 1 wherein said additive is paraffin wax.

4. The method of claim 1 wherein said emulsion includes said fungal pathogen.

5. The method of claim 1 wherein said emulsion includes calcium hydroxide.

6. The method of claim 2 wherein said emulsion includes calcium hydroxide.

7. The method of claim 3 wherein said emulsion includes calcium hydroxide.

8. A formulation for applying fungal pathogen to undesirable host vegetation comprising a water-in-oil invert emulsion containing said fungal pathogen and an additive that enables water which reaches said vegetation to remain thereon with minimal loss through evaporation, thereby supplying necessary moisture for fungal germination and growth, said additive selected from the group consisting of (a) a wax selected from the group consisting of paraffin wax, beeswax and natural plant wax, (b) lecithin in combination with calcium chloride or acetate, and (c) mixtures of (a) and (b).

9. The formulation of claim 8 wherein said additive is paraffin wax.

10. The formulation of claim 8 wherein said additive is lecithin and calcium chloride.

11. The formulation of claim 8 including calcium hydroxide therein.

12. The method of claim 1 wherein said fungal pathogen is selected from the group consisting of *Colletotrichum gloeosporioides, Colletotrichum malvarum, Fusarium lateritium, Fusarium solani, Alternaria macrospora, Alternaria cassiae,* and *Alternaria crassa.*

13. The method of claim 1 wherein said water-in-oil emulsion is applied immediately after application of said fungal pathogen.

14. The formulation of claim 8 wherein said fungal pathogen is selected from the group consisting of *Colletotrichum gloeosporioides, Colletotrichum malvarum, Fusarium lateritium, Fusarium solani, Alternaria macrospora, Alternaria cassiae,* and *Alternaria crassa.*

15. The method of claim 13 wherein said emulsion includes calcium chloride and lecithin.

16. The method of claim 13 wherein said emulsion includes paraffin wax.

17. The method of claim 13 wherein said fungal pathogen is selected from the group consisting of *Colletotrichum gloeosporioides, Colletotrichum malvarum, Fusarium lateritium, Fusarium solani, Alternaria macrospora, Alternaria cassiae,* and *Alternaria crassa.*

18. The method of claim 1 wherein said additive is paraffin wax, lecithin and calcium chloride.

19. The formulation of claim 8 wherein said additive is paraffin wax, lecithin and calcium chloride.

* * * * *